United States Patent [19]

Cewers et al.

[11] Patent Number: 4,616,801
[45] Date of Patent: Oct. 14, 1986

[54] APPARATUS TO REGULATE THE FLOW OF LIQUIDS

[75] Inventors: Goeran Cewers, Lund; Jan Johansson, Esloev; Sven-Gunnar Olsson, Soedra, all of Sweden

[73] Assignees: Siemens Elema AB, Solna, Sweden; Siemens Aktiengesellschaft, Berlin and Munich, Fed. Rep. of Germany

[21] Appl. No.: 572,712

[22] Filed: Jan. 20, 1984

[30] Foreign Application Priority Data

Jan. 24, 1983 [DE] Fed. Rep. of Germany ....... 3302214

[51] Int. Cl.⁴ .................. F16L 55/14; F16K 51/00
[52] U.S. Cl. .......................................... 251/6; 251/9; 604/250
[58] Field of Search ............... 251/6, 9; 604/34, 250, 604/253

[56] References Cited

U.S. PATENT DOCUMENTS

| | | | |
|---|---|---|---|
| 4,261,388 | 4/1981 | Shelton | 604/253 |
| 4,294,248 | 10/1981 | de Figueiredo | 604/31 |
| 4,397,642 | 8/1983 | Lamadrid | 251/9 |
| 4,452,273 | 6/1984 | Hanzawa et al. | 604/253 |
| 4,460,358 | 7/1984 | Somerville et al. | 604/250 |
| 4,493,710 | 1/1985 | King et al. | 604/250 |

FOREIGN PATENT DOCUMENTS 2021290 11/1979 United Kingdom .

Primary Examiner—George L. Walton
Attorney, Agent, or Firm—Thomas H. Jackson

[57] ABSTRACT

In order to be able to regulate in a simple and reliable manner the quantity of liquid that is administered to a patient through a hose in an infusion device, there is provided, according to the invention, a motor-driven eccentric, which presses the hose against a blocking device and clamps it off to a greater or lesser degree. The blocking device forms a part of at least one guide for the hose and can assume two positions. In one of the positions the guide is released; in the other position it is closed. A lever mounted with freedom to rotate, which can be spring-loaded, is particularly well suited for the blocking device. In addition, a clamping lever which can be activated through an electromagnetic latch, can be provided as an emergency stop.

18 Claims, 9 Drawing Figures

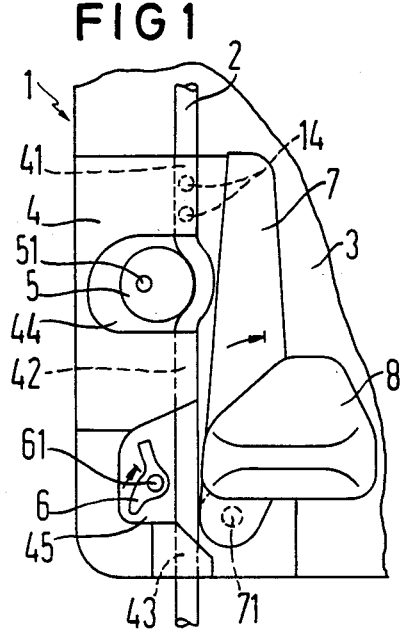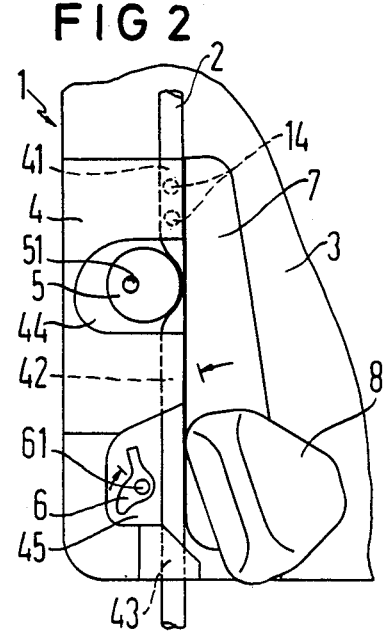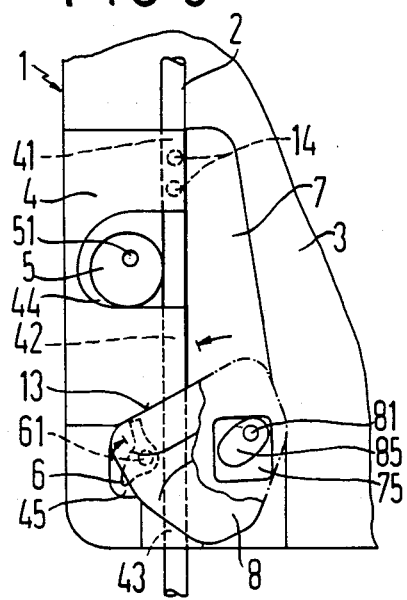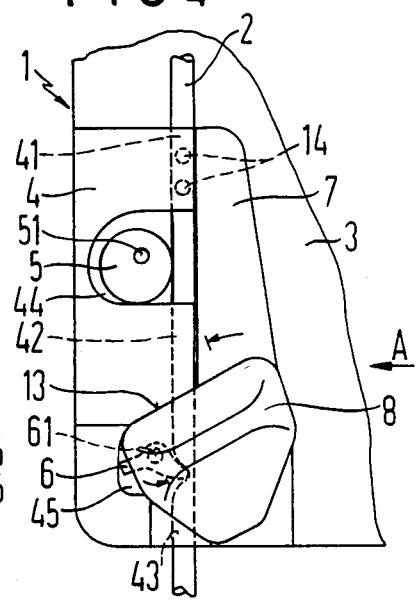

APPARATUS TO REGULATE THE FLOW OF LIQUIDS

BACKGROUND OF THE INVENTION

The invention relates to apparatus for regulating the flow of liquids, such as infusion liquids, through a hose. The apparatus includes a part that moves in the direction of the hose, such as a motor-driven eccentric, a blocking device, and at least one guide for the hose.

In existing infusion devices, the infusion liquid is continuously fed into a patient through a hose. As a result of the vacuum created by the gravitational force of the discharged liquid, the hose is filled up with liquid drop by drop from a reservoir container. The drops can be detected and used to regulate the volume of flow. It is known from U.S. Pat. No. 4,294,248, that this method can be used to regulate both the amount of liquid that is delivered to a patient and the period during which this amount is to be delivered. In order to change the rate of flow in this case, a motor-driven clamping device, such as an eccentric is used, which allows the inner cross-section of the hose to be released to a greater or lesser extent. Particularly when an infusion device is used on patients who must be connected by the nursing staff to the hose, the staff must also be able to operate it correctly.

SUMMARY OF THE INVENTION

The object of the invention is to provide apparatus of the type already described, which is simple enough to ensure perfect operation without great effort in all cases, and which fulfills the strict safety requirements imposed on health care equipment.

It is another object of the invention to provide apparatus which is practically immune to operational failure of the flow regulation.

It is still a further object of the invention to provide apparatus which can control flow regulation simultaneously with the control of other functions of an infusion device, without much additional effort.

These objects are accomplished according to the invention, by having the blocking device in the arrangement be part of the guide for the hose and be capable of taking at least two positions. In one position the guide is released, and in the other position it is closed. It is particularly advantageous for this purpose to utilize a first layer, mounted with freedom to rotate, as a blocking device. By means of this movable blocking device, the guides that are provided for the hose can be released in a single operation, and simultaneously a gap between the hose and, for example an eccentric, can be enlarged to the point where the hose can be inserted quickly and easily. If the blocking device is moved back to its starting position, the guides are closed so that the hose is held fast in the predetermined position, and the blocking device is brought at the same time into the correct position for it to be able to change the inner cross-section of the hose with the aid of the eccentric.

In the case when the blocking device is a first lever mounted with freedom to rotate, an advantageous refinement of the apparatus can be obtained by providing this first lever outside its axis with a notch into which a second lever, which can be activated by means of a handle, fits with freedom to move. In this case the notch and the second lever should be designed in such a way that the latter is free to move in the notch over a specific angular range. However, when it exceeds that angular range in either direction it carries the first lever into the respective opposite position. In order to ensure that the first lever also remains in the correct closed position, a further refinement of the invention provides that this first lever is spring-loaded in such a way that a force is exerted in the direction that closes the guide.

In addition, it can be provided with an electrical switch that can be activated by the first lever. In addition, the second lever can be spring-loaded in such a manner that it can assume two defined positions within the angular range in which it is free to move. In this manner, the second lever can, for practical purposes, be brought into three specific positions. In the first position, the first lever releases the guides so that the hose can be inserted or removed. In the second position the guides are closed due to the pressure of the spring on the first lever, and the first electrical switch is activated. In this position, it is possible for practical purposes, to check the entire system once again, prior to the flow being released. In the third position, the second lever activates another electrical switch which might, for example, be a position switch for a motor to drive the eccentric. As long as this switch is not activated, the eccentric is in a position such as to completely clamp off the hose. Not until this switch is activated is the eccentric released, so that it can now assume a position corresponding to the desired volume of flow. The second lever, too, can be spring-loaded. In this case, the spring force applied can alternatively support the closing motion and the opening motion of the first lever.

A refinement that substantially increases the safety of the arrangement, and thereby of the entire infusion apparatus, provides that in the vicinity of the blocking device there is mounted a rotating clamping lever and between this clamping lever and the blocking device the hose is introduced. In this case, during normal operation this clamping lever is held by a latch in such a position that the flow of liquid through the hose is not impeded. In emergencies in which the flow of liquid must be cut off abruptly to avoid danger to the patient, this latch is lifted and the clamping lever is pressed by a large force against the hose so that the flow of liquid is instantly cut off. A conceivable emergency would be, for example the malfunctioning of the eccentric or a total power failure.

To keep energy consumption as low as possible, particularly in battery-operated devices, the latch includes a tappet that is held in the latch position by a spring and can be withdrawn from this position by means of an electromagnet. Therefore, electrical energy in this case is only used to undo the latch. To ensure that the latch functions reliably even when the batteries fail, a capacitor can be provided whose stored load constitutes a sufficient emergency source. Another possible emergency might, for example, consist of gas bubbles in the stream of liquid in the system. A particularly space-saving design is obtained if a bubble detector is integrated into the arrangement, particularly in the vicinity of a guide. The signals from this bubble detector can then in turn be used to undo the latch. In view of the fact that not even the first detected gas bubble should reach the patient, the bubble detector should be placed before the clamping lever in the line of flow.

Again from the pont of view of energy-saving, it is advisable for the clamping lever to be spring-loaded in such a way that in the position in which the hose is released, only a very short power arm is effective for the activating force. This ensures that only minimal energy is consumed in releasing the latch.

To keep the arrangement as simple as possible, and to facilitate the insertion and removal of the hose, it is advisable to make all the guides approximately straight. This allows the hose to be quickly and easily inserted in its extended position. Nevertheless, in order to guard against incorrect insertion, the entire arrangement, except for the guides and the space that is necessarily left free for the eccentric or the clamping lever, should be filled with material so that improper positioning of the hose is completely precluded.

Other features and advantages of the invention will be apparent from the following detailed description and from the claims.

For a full understanding of the present invention, reference should now be made to the following detailed description and to the accompanying drawings.

BRIEF DESCRIPTION OF THE DRAWINGS

FIGS. 1–4 show schematically a front view of a section of an infusion device in four different situations or states.

DETAILED DESCRIPTION

Figure 5:
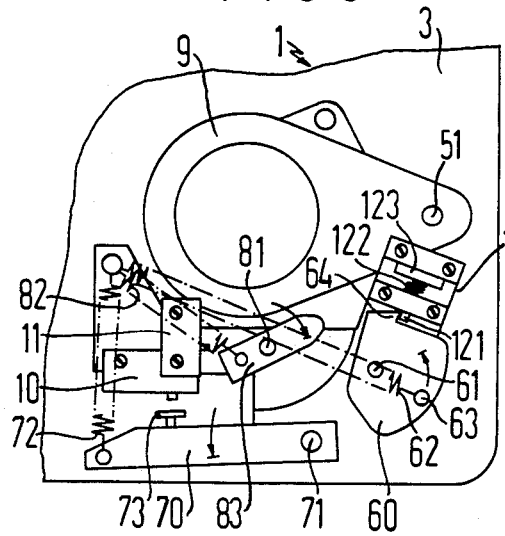
FIGS. 5–8 show a rear view corresponding to the views shown in FIGS. 1–4, respectively.

FIG. 1 shows a section of infusion device 1 for feeding infusion liquid into a patient (not shown) through hose 2. At its upper end, the hose can be attached to a reservoir vessel, from which liquid is withdrawn in drops. The drops can be recorded in a conventional manner by means of a detector, and can be used to control the rate of flow. The arrangement shown in this embodiment includes plastic part 4, which is mounted on front plate 3 of device 1. Plastic part 4 has a row of guide slots 41, 42 and 43 as well as two recesses 44 and 45. Located in recess 44 is eccentric 5 whose axis is designated as 51. In recess 45 is located clamping lever 6. Opposite to plastic part 4 is lever 7, mounted with freedom to rotate, which serves as a blocking device for eccentric 5 and clamping lever 6 as well as guides 41, 42 and 43. Axis 71 of this lever 7 is shown by the broken lines. Also shown in FIG. 1 is handle 8 which can be used to move lever 7 into two positions. Handle 8 also serves other purposes which are described in greater detail in connection with the other figures.

As already explained, eccentric 5, controlled by a drop detector and driven by a motor, can be used in a conventional manner to regulate the flow. FIG. 5 is a rear view, showing those parts of the arrangement that are mounted on the rear of housing plate 3. This view shows motor 9 that drives eccentric 5; only axle 51 of eccentric 5 that passes through it can be seen in this representation. Also shown are axle 61 that passes through clamping lever 6 and axle 81 of handle 8; a front view of the latter is given in the partially cut-off view in FIG. 3.

In addition, two electrical switches 10 and 11 and latching device 12 are represented. As can be seen from FIG. 5, lever 7 continues on the back of front plate 3 with an approximately right-angled part 70. At the end of part 70 is attached spring 72. The force of spring 72 brings lever 7 into the closed position, which is the position in which guides 41 to 43 are covered by lever 7. Part 70 also serves to activate switch 10 through contact 73.

Clamping lever 6 also has extension 60 on the rear side, to which spring 62 is attached at point 63. In addition, part 60 has at its upper end catch 64, into which rod 121 loaded with a spring 122 can fit. By this means part 60 and, as a result, clamping lever 6 are held in the positions shown in FIGS. 1 and 5 respectively, although the force of spring 62 tends to move it out of this position. As can further be seen from this Fig., the power arm for the applied spring force is very short, so that in this rest position only a very small force is needed to keep lever 6 in this position. Latch 12 has, in addition, electromagnet 123, which can be activated by a small current pulse in such a manner that rod 121 is moved contrary to the force of spring 122, and releases the catch and as a result clamping lever 6. The latch thereby fulfills an essential requirement for the entire apparatus, namely to operate with extremely low energy consumption so that even when the device is battery-operated it has the longest possible useful life.

By means of a capacitor connected in front of magnet 123, it is possible, for example to store enough energy to ensure that this latch can be released even in the event of a total power failure.

Figure 7:
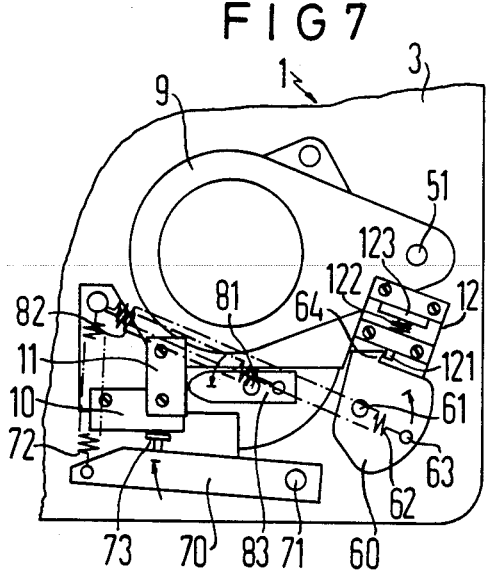
Figure 8:
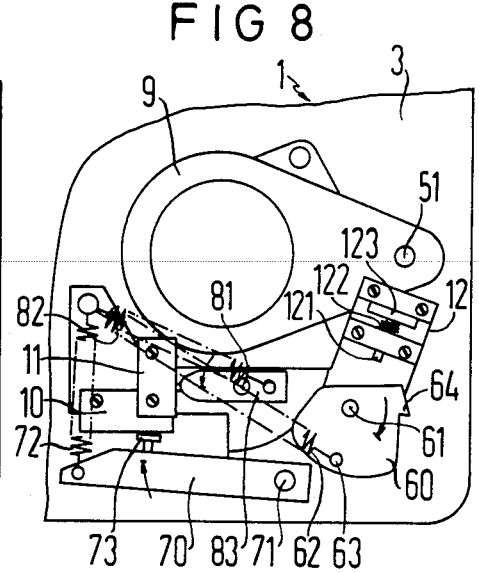

It can also be seen from FIG. 5, that handle 8 has on the rear side of housing plate 3 a part 83 that rotates about axle 81, on which force is also exerted by means of spring 82. By means off this part 83 (as shown in FIGS. 7 and 8) switch 11 can be activated. In addition, spring 82 acts on part 83 so that it can be brought into two predetermined positions, in which case the spring extends beyond axle 81.

Figure 6:
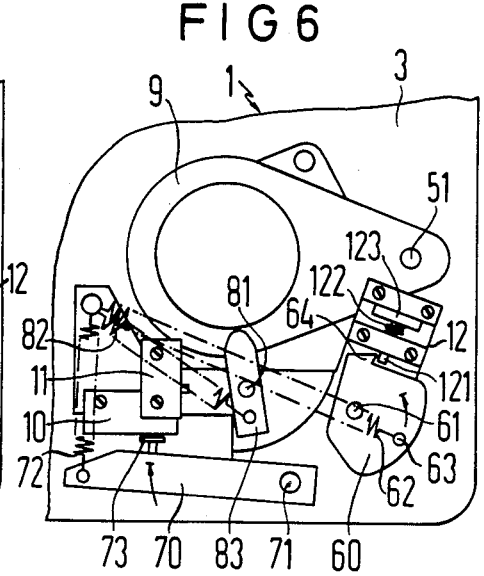

FIGS. 2–4 and 6–8 show the same arrangement in various positions, while FIG. 1 shows the open position, in which hose 2 can be inserted in the arrangement or removed from it. FIGS. 2 and 6 show a position in which guides 41 to 43 are already closed, and switch 10 has been activated, but switch 11 has not yet been turned on.

FIGS. 3 and 7 show a position in which the handle has been turned still further to stop 13. In this case clamping lever 6 is covered by a part of the handle, so that the latter is out of reach. Also shown in FIG. 3 as a result of the partially cut-off representation, are axle 81 of handle 8 and a lever or eccentric 85 that is connected with the latter, and which is located in notch 75 of lever 7. As can be seen from this illustration, eccentric 85 is free to move in notch 75 through a certain angular range which is roughly determined by the positions of handle 8 in FIGS. 2 and 3. If handle 8 is turned further, beyond this angular range, lever 7 will be deflected.

In the Figs. discussed thus far, it has been shown in each case that clamping lever 6 is latched, and accordingly does not interfere with the flow of liquid. Now in FIGS. 4 and 8, a situation is represented in which the latch has just been released and lever 6 is completely clamping off hose 2 so that the transport of liquid is totally prevented. As can be seen from FIG. 8, in this case a relatively large power arm is effective for acting spring 62 so that lever 6 is pressed against the hose with a sufficiently large force.

In the vicinity of guide 41, two bubble detectors are located, which release the latch if a gas bubble occurs in the liquid.

Figure 9:
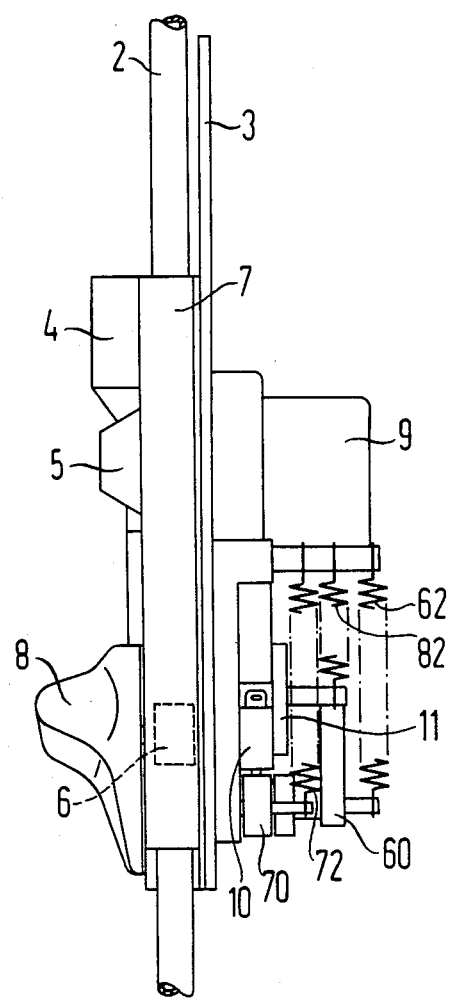
FIG. 9 shows a side view in the direction of arrow A shown in FIG. 4.

Finally, the schematic side view shown in FIG. 9 is simply intended to make it clear that a space-saving arrangement of all the parts can be achieved in a particularly favorable manner, if they are arranged above one another on several levels. In this case again, only the parts on one side of front housing plate 3 are visible and accessible to the operator. In FIG. 9, these are the parts to the left of this plate.

The apparatus operates in accordance with the invention as follows:

In the position shown in FIGS. 1 and 5, the arrangement can be loaded, so that hose 2 can be inserted into the arrangement in a simple manner. Guides 41 and 43 ensure that the position of the hose in the arrangement is precisely determined. It is highly desirable to design recesses 44 and 45 so that there is no possibility of the hose passing by eccentric 5 or clamping lever 6 in an improper manner. As FIG. 5 shows, both switches 10 and 11 are still open. If handle 8 is now rotated by approximately 90°, eccentric 85 releases lever 7, so that it is pressed by spring 72 against the guides, which are closed as a result. At the same time switch 10 is activated, and the arrangement is electrically turned on, but not yet put into operation, since switch 11 has not yet been activated. This switch is a so-called position switch, which ensures, in its unactivated condition, that motor 9 brings the eccentric into a position such that the hose is completely clamped off at that point. Not until handle 8 is turned further, and switch 11 is activated, in which case the handle simultaneously covers clamping lever 6, is the motor control released in order to adjust the flow to a predetermined value.

With the aid of this arrangement in accordance with the invention, it is possible by means of a simple handle, mounted with freedom to rotate, to execute several functions specifically and reliably, which substantially simplifies the actions to be performed by the operating personnel. In addition, this arrangement permits a decisive improvement in operating safety, and thus eliminates risks for the patients resulting from an uncontrolled administration of liquid or from dangerous bubbles. In addition, the arrangement also meets the requirement of operating with a minimum consumption of energy, despite the additional safety devices, such as clamping lever 6.

In the embodiment shown, lever 7 not only forms a part of the guides 41, 42, 43, but also the blocking device for eccentric 5 and clamping lever 6. Other embodiments are conceivable within the frame-work of the invention, in which, for example, a separate blocking device is provided for eccentric 5 and/or clamping lever 6.

There has thus been shown and described an apparatus for regulating the flow of liquids which fulfills all the objects and advantages sought therefor. Many changes, modifications, variations and other uses and applications of the subject invention will, however, become apparent to those skilled in the art after considering the specification and the accompanying drawings which disclose preferred embodiments thereof. All such changes, modifications, variations and other uses and applications which do not depart from the spirit and scope of the invention are deemed to be covered by the invention which is limited only by the claims which follow.

What is claimed is:

1. An apparatus for regulating the flow of liquid through a hose, comprising:
   means for guiding the hose comprising at least one guide for supporting and engaging at least a portion of the hose; means for clamping the hose, including a motor-driven eccentric; and a pivotal blocking device forming a separate part of the hose guiding means from the at least one guide, as well as forming a part of the clamping means, the blocking device being pivotal between a closed position, in which position the at least one guide cooperates with the closed blocking device so that the at least portion of hose is safely and completely enclosed between the hose guiding means and the pivotal blocking device, which portion of hose may or may not be clamped shut, and the closed blocking device further cooperates with the motor-driven eccentric for controlling the cross-section of the hose, and an open position in which the hose is released when the pivotal blocking device no longer cooperates with the at least one guide to completely enclose the at least portion of hose.

2. The apparatus according to claim 1, wherein the pivotal blocking device includes a first lever mounted with freedom to pivot.

3. The apparatus according to claim 2, further comprising a second lever and a handle for rotating the second lever, the first lever including outside its pivotal axle a notch receiving the second lever, the notch and the second lever being designed so that the second lever is free to rotate through a specified angular range in the notch while the first lever is in the closed position, the second lever carrying the first lever into the open position when the second lever exceeds said range.

4. The apparatus according to claim 3, further comprising a clamping lever mounted operationally adjacent to the blocking device and rotatable between first and second positions, a clamping lever spring biasing the clamping lever, a further guide for guiding the hose between the clamping lever and the blocking device, and a latch for holding the clamping lever in the second position, whereby in the first position the clamping lever completely clamps off the hose, with a large power arm being effective for the clamping lever spring, and in the second position the hose is released, with only a very small power arm being effective for the clamping lever spring.

5. The apparatus according to claim 4, further comprising a second electrical switch which is activatable by the second lever.

6. The apparatus according to claim 2, wherein the first lever is biased by a first spring so that a force is exerted in a direction tending to move the blocking device into its closed position.

7. The apparatus according to claim 2, further comprising a first electrical switch that can be activated by the first lever.

8. The apparatus according to claim 3, wherein the second lever is biased by a second spring so that the second lever can assume two specified positions within the specified angular range in which it is free to rotate without moving the first lever into an open position.

9. The apparatus according to claim 8, wherein, when the second lever is switched between the two specified positions, the second spring sweeps over the rotation axle of the second lever.

10. The apparatus according to claim 8, wherein the force exerted on the second lever partially supports the closing movement of the first lever into its closed position and its opening movement into its open position.

11. The apparatus according to claim 9, where the force exerted on the second lever partially supports the closing movement of the first lever into its closed position and its opening movement into its open position.

12. The apparatus according to claim 3, further comprising a second electrical switch that can be activated by the second lever.

13. The apparatus according to claim 1, further comprising a clamping lever mounted operationally adjacent to the blocking device and rotatable between first and second positions, a clamping lever spring biasing the clamping lever, a further guide for guiding the hose between the clamping lever and the blocking device, and a latch for holding the clamping lever in the second position, whereby, in the first position, the clamping lever completely clamps off the hose, with a larger power arm being effective for the clamping lever spring, and, in the second position, the hose is released, with only a very small power arm being effective for the clamping lever spring.

14. The apparatus according to claim 13, wherein the latch comprises a tappet, biased by a further spring, for holding the clamping lever in its second position and is drawn out of position by means of an electromagnet.

15. The apparatus according to claim 13 wherein, when the first lever is in the closed position, the second lever activates the second electrical switch and the clamping lever is covered by the handle.

16. The apparatus according to claim 14, further comprising a bubble detector, mounted in the vicinity of at least one guide, which activates the electromagnet in accordance with the signals received.

17. The apparatus according to claim 16, wherein said bubble detector is mounted in front of the clamping lever with regard to the line of flow of the liquid.

18. The apparatus according to claim 1, wherein, in the event there are two or more guides provided, the guides are aligned for guiding the hose in a straight line through the apparatus.

* * * * *